United States Patent
Balkovec et al.

Patent Number: 5,159,059
Date of Patent: Oct. 27, 1992

[54] PROCESS FOR REDUCTION OF CERTAIN CYCLOHEXAPEPTIDE COMPOUNDS

[75] Inventors: James M. Balkovec, North Plainfield; Regina C. Black, Cranford, both of N.J.

[73] Assignee: Merck & Co., Inc., Rahway, N.J.

[21] Appl. No.: 529,295

[22] Filed: May 29, 1990

[51] Int. Cl.$^5$ .................... A61K 37/02; C12P 21/04
[52] U.S. Cl. ................................. 530/317; 530/345; 435/71.3; 435/913
[58] Field of Search ............... 530/317, 345; 435/71.1, 435/71.3, 913

[56] References Cited

U.S. PATENT DOCUMENTS 4,559,339  12/1985  Bock et al. ............................ 514/219

OTHER PUBLICATIONS

J. Auerbach et al., J. Org. Chem. 41, 725 (1976).
von R. Traber et al., Helv. Chim. Acta, 62, 1252 (1979).

Primary Examiner—John Doll
Assistant Examiner—Bennett Celsa
Attorney, Agent, or Firm—Alice O. Robertson; Hesna J. Pfeiffer

[57] ABSTRACT

Process for producing a compound of the formula

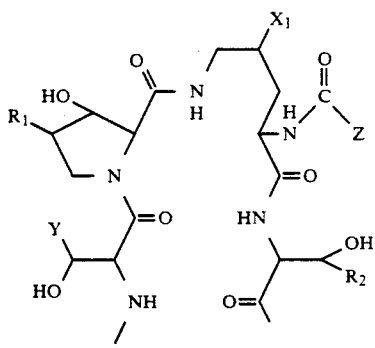

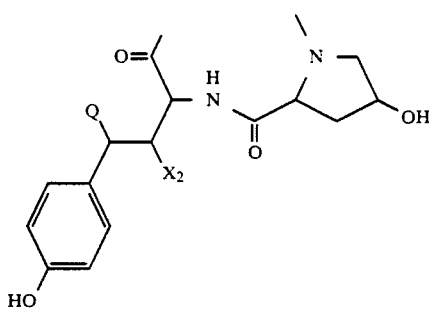

by selectively reducing a compound of the formula

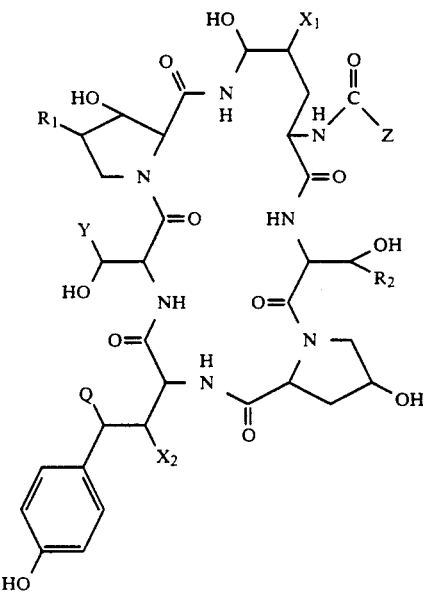

in a strong acid medium with excess molar equivalent of reducing agent so that the OH adjacent to $X_1$ is reduced to H and if Q is OH in the starting material, it optionally may be reduced H.

5 Claims, No Drawings

PROCESS FOR REDUCTION OF CERTAIN CYCLOHEXAPEPTIDE COMPOUNDS

BACKGROUND OF THE INVENTION

Echinocandins and echinocandin-like cyclohexapeptide compounds are described in the literature as highly effective antifungal agents, particularly against yeasts causing mycotic infections such as *Candida albicans*, *Candida parapsilosis* and the like. Some of these compounds are natural products produced by cultivation of microorganisms such as *Aspergillus rugulosus*, *Aspergillus nidulans* or *Acrophialophoria lemonispora* described in U.S. Pat. Nos. 4,024,245, 4,024,246 and 4,173,629, respectively. Some of these compounds are semi-synthetic obtained by modifying the natural products such as described in U.S. Pat. Nos. 4,287,120, 4,293,487, 4,293,489, 4,320,053, 4,370,054 and 4,322,338. The latter semi-synthetic compounds were generally prepared by deacylating the lipophilic side chain attached to an amino substituent on the cyclohexapeptide nucleus and thereafter reacylating to obtain modified cyclopeptides in which the lipophilic side chain was different but in which the cyclohexapeptide nucleus stayed basically the same.

The echinocandin type cyclohexapeptide compounds are generally unstable in aqeuous medium. During a search for echinocandin type cyclohexapeptide compounds, it was found that modifying the formula by reducing certain hydroxyl groups would produce a more stable compound. In Helvetica Chimica Acta 62, 1252, 1267 (1979), there is described reduction of certain hydroxyl groups in tetrahydroechinocandin B and tetrahydroechinocandin C. It is, however, a multistep procedure and, a selective reduction has not been demonstrated. Thus, when tetrahydroechinocandin B is the starting material, a bis-reduced product is obtained by a two step procedure in which the thioether intermediate must be isolated and thereafter reduced:

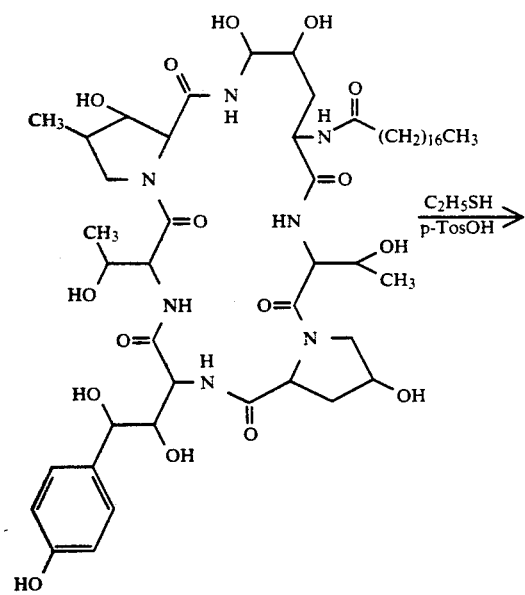

STATEMENT OF THE INVENTION

According to the present invention, there has been discovered an improved process for selectively reducing certain hydroxyl groups in echinocandin type cyclohexapeptide compounds to obtain deoxycyclohexapeptide compounds which may be totally novel or may be a minor natural product not obtainable in significant quantities.

DESCRIPTION OF THE INVENTION

According to the present invention, an echinocandin type cyclohexapeptide compound which is represented by the formula

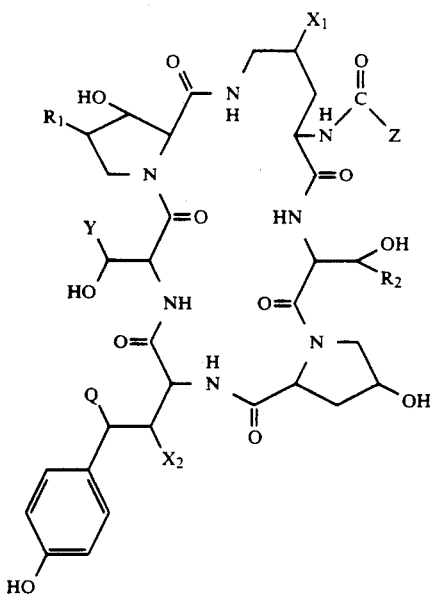
(I)

may be facilely produced by intimately contacting an echinocandin type cyclohexapeptide compound represented by the formula

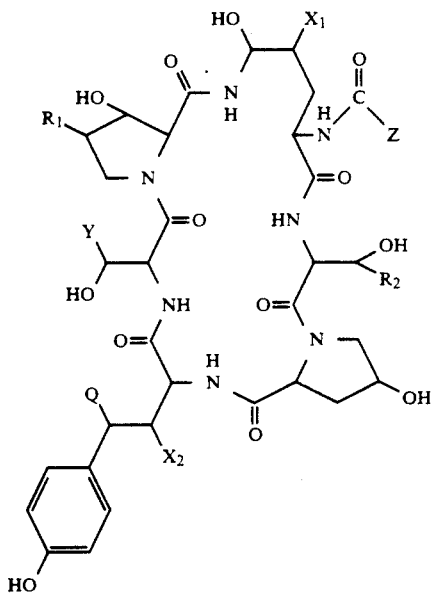
(A)

in a strong acid medium with a reducing agent for time for reaction to take place with the formation of the desired product.

In the foregoing and subsequent formulas
Q is hydrogen or hydroxyl,
$R_1$ and $R_2$ are independently hydrogen or methyl,
$X_1$ and $X_2$ are independently hydrogen or hydroxyl,
Y is H—, $CH_3$— or —$CH_2CONH_2$ and
Z is (a) a straight or branched chain alkyl from 5 to 23 carbon atoms, (b) a straight or branched chain alkenyl from 5 to 23 carbon atoms, (c) phenyl and substituted phenyl wherein the substituent is $C_1$ to $C_{16}$ alkyl, $C_1$ to $C_{16}$ alkoxy, $C_2$ to $C_{20}$ alkanoylamino, or $C_1$ to $C_{16}$ thioalkoxy; or (d) heteroaryl selected from the group consisting of pyrryl, thiophenyl, furyl, indolyl, benzothiophenyl, benzofuryl, imidazolyl, benzimidazolyl, and pyridinyl.

Representative groups when Z is alkyl are normal and branched heptadecyl, nonyl, nonadecyl, heptyl, tridecyl, 9,11-dimethyltridecyl, pentadecyl and the like.

Representative groups when Z is alkenyl are 8,11-heptadecadienyl, 2-pentenyl, 4-heptenyl, 7-pentadecenyl, 8-heptadecenyl, 10-heptadecenyl and the like.

Representative groups when Z is aryl and substituted aryl are phenyl, tolyl, xylyl, 2-ethylphenyl, 4-ethylphenyl, 4-isopropylphenyl, 4-isooctylphenyl, 4-tert-butylphenyl, 4-decylphenyl, 3-ethoxyphenyl, 4-isopropoxyphenyl, 4-(n-nonyloxy)-phenyl, 4-(n-octyloxy)phenyl, 4-(n-decyloxy)phenyl, 2,4-dimethoxyphenyl, 4-(t-butoxy)phenyl, 2-methylthiophenyl, 4-(n-nonylthio)phenyl, 4-(n-octylthio)phenyl, mesityl, 4-(n-heptanoylamino)phenyl, 4-(n-decanoylamino)phenyl, 4-(n-hexadecanoylamino)phenyl, and the like.

Representative groups when Z is heteroaryl are 2-pyrryl, 3-pyrryl, 2-furyl, 3-furyl, 2-pyridinyl, 3-pyridinyl, 4-pyridinyl, 2-indolyl, 2-benzofuryl, 2-benzimidazolyl, 2-imidazolyl, thiophene-2-yl, and the like.

The preferred compounds are those in which Z is alkyl and alkenyl from 9 to 17 carbon atoms, substituted phenyl wherein the substituent is $C_4$ to $C_{10}$ alkyl, alkoxy, or thioalkoxy, or $C_{10}$ to $C_{18}$ alkanoylamino.

When Q in the starting material (formula A) is OH, it may be reduced to form a bis reduced product which may be represented by the formula

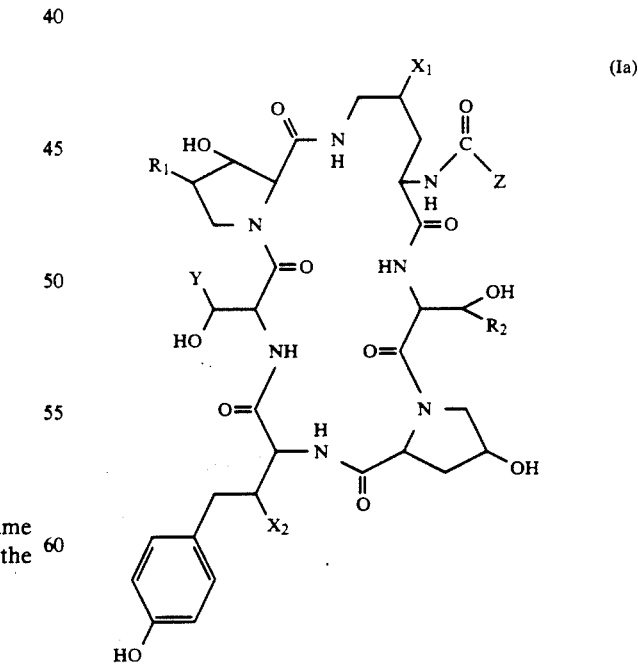
(Ia)

or it may be reduced to form a mono-reduced product which may be represented by the formula

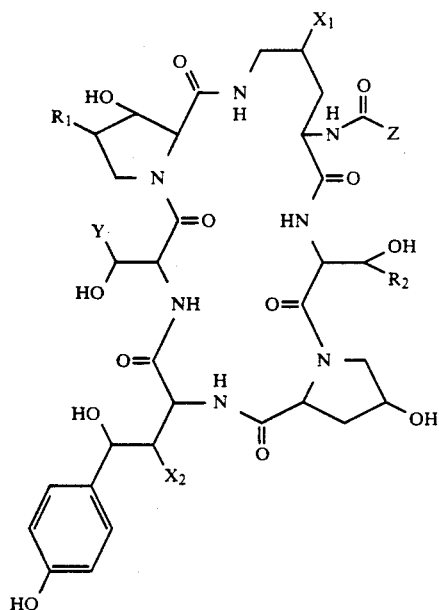
(Ib)

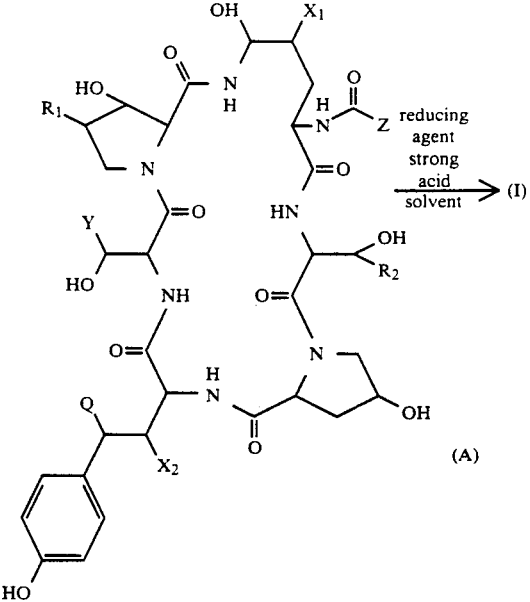
(A)

$$\xrightarrow[\text{solvent}]{\substack{\text{reducing}\\ \text{agent}\\ \text{strong}\\ \text{acid}}} \text{(I)}$$

When Q is H, but the other groups are otherwise the same, the compound of formula (Ia) may be obtained under mono-reduction conditions. A mono-reduction by-product of the formula (Ic)

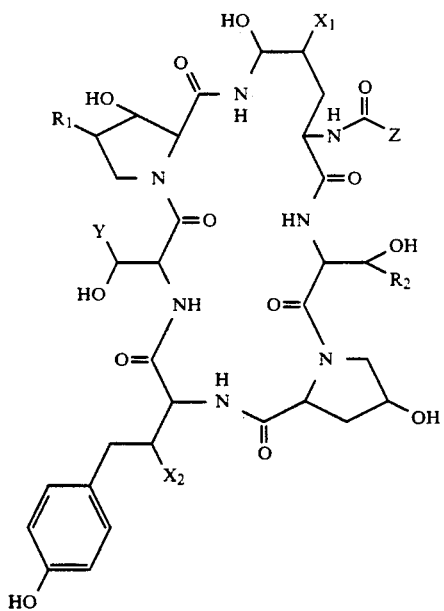
(Ic)

also may be obtained but is separable from (Ib) by subjecting the reaction product to alcoholic medium in which (Ic) is unstable.

The process of the present invention may be represented by the following equation:

The starting materials are natural products or semi-synthetic compounds obtained by the modification of the natural products. The starting materials which are semi-synthetic compounds, are generally those in which Z has been modified and are prepared by enzymatic deacylation of a natural product to obtain a deacylated nucleus and thereafter reacylating with Z-COCl as described in the literature and subsequently detailed. Compounds obtained by the reduction of the starting materials in which $R_1$, $R_2$ and Y in the nuclei are in the following arrangement

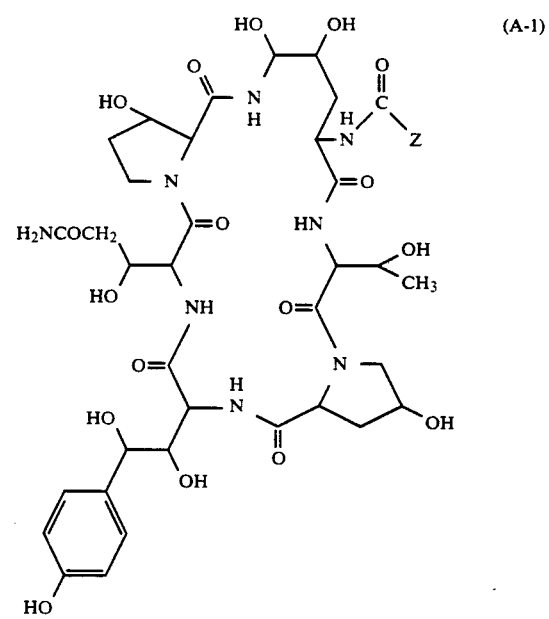
(A-1)

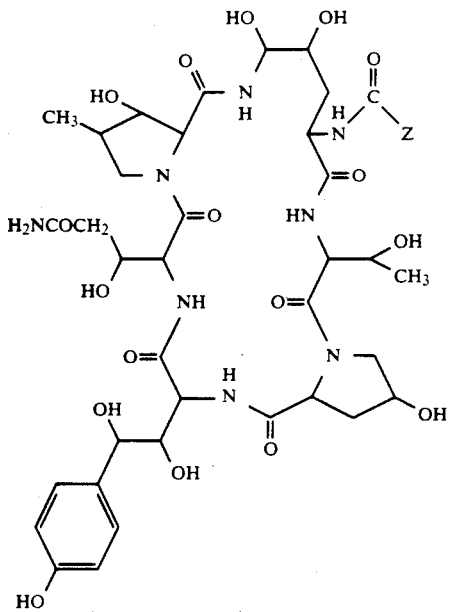
(A-2)

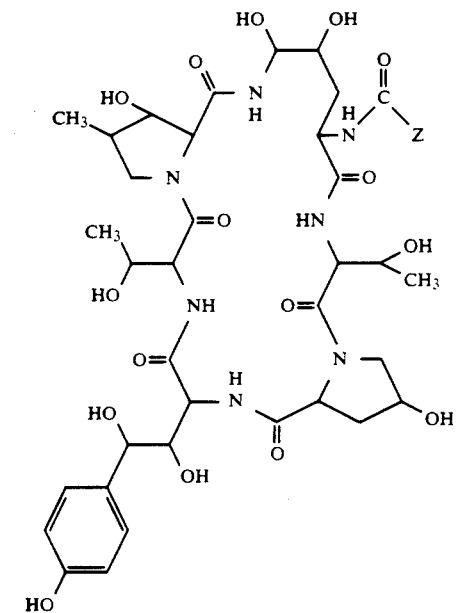
(A-3)

are of most interest and the invention is illustrated primarily employing these starting materials although other starting materials available or preparable as subsequently described may be employed.

The reducing agents are selected from those which are stable in an acid environment. Representative reducing agents are sodium cyanoborohydride, triethyl silicon hydride and sodium borohydride. Especially preferred is sodium cyanoborohydride.

The reaction is carried out in the presence of a strong acid. Suitable strong acids include trifluoroacetic acid and trichloroacetic acid. With trichloroacetic acid, a halohydrocarbon solvent such solvent as methylene chloride is employed.

The product of the reduction may be a bis-reduced product or a mono-reduced product. When it is desired to obtain a mono-reduced product, namely, a product in which Q is OH in formula (I), a solvent is employed. The solvent may be protic or aprotic such as methylene chloride or other halohydrocarbon. The preferred solvent for obtaining a mono-reduced product is glacial acetic acid.

When a bis-reduced product, Q in formula (I) is H, is desired, a separate solvent may not be necessary. The strong acid such as trifluoroacetic acid serves as a suitable reaction medium.

The reaction may be summarized as follows:

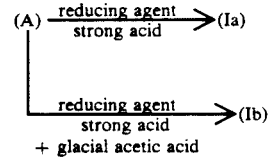

In carrying out the reaction to obtain Compound Ia, the lipopeptide is dissolved in the strong acid and to the resulting solution, is added the reducing agent while stirring at ambient temperature. Usually, the reaction takes place immediately, but stirring is continued for from about 0.5 to 4 hours to insure completion of the reaction and the formation of Compound Ia. At the end of this period, the volatiles are removed under reduced pressure to obtain a residue which is subjected to reverse phase chromatography employing water/acetonitrile as eluant and to obtain a purified product from the appropriate fractions determined with the aid of NMR.

When the desired product is the mono-reduced product, essentially the same procedure is employed except that the reactant lipopeptide is first dissolved in glacial acetic acid or other solvent. Thereafter, the acid is added followed by the reducing agent until the mono-reduced product is formed. This can be determined by a high performance liquid chromatography assay combined with an NMR determination. The product may be recovered and purified in the same manner as for the bis-reduced product.

The products of the process of the present invention retain all or substantially all of the antiparasitic properties, particularly antifungal properties, possessed by the starting materials, but have the property of stability in aqueous media, not possessed by the starting materials. Thus, the process of the present invention produces compounds which may be utilized in therapeutic application not practical with the parent compounds.

The antifungal activity of the echinocandins are well known. The reduced compounds also have similar activity. The compounds also have activity, as antiparasitic agents with novel and useful properties of inhibiting or alleviating *Pneumocystis carinii* infections. The latter property of many of the compounds has been described in copending applications Ser. No. 495,878, and Ser. No. 495,652 both filed Mar. 19, 1990.

Representative of the latter utility is the efficacy of Compound I in which $R_1$ is H, $R_2$ is $CH_3$, Q is H, $X_1$ and $X_2$ are OH, Y is $CONH_2$ and Z is 9,11-dimethyltridecyl (herein referred to as Compound Ia).

In a representative study with Compound Ia, Sprague-Dawley rats (weighing approximately 250 grams) were immunosuppressed with dexasone in the drinking water (2.0 mg/L) and maintained on a low-protein diet for five weeks to induce the development of pneumocystis pneumonia from a latent infection. Before drug treatment 2 rats were sacrificed to confirm the presence of *Pneumocystis carinii* pneumonia (PCP); both rats were found to have infections. Five rats (weighing approximately 150 grams) were injected intraperitoneally (IP) twice daily for four days with Compound Ia in 0.25 ml of 10% dimethylsulfoxide (DMSO) to supply drug at 0.6, 1.2 and 2.5 mg/kg of body weight. Control animals received 10% DMSO alone. All animals continued to receive dexasone in the drinking water and low protein diet during the treatment period. At the completion of the treatment, all animals were sacrificed, the lungs were removed and processed, and the extent of disease determined by microscopic analysis of stained slides. The results of the study showed that Compound Ia was effective in eliminating *P. carinii* cysts in four days with an $ED_{90}$ between 0.6 and 1.2 mg/kg.

The following examples illustrate the invention but are not to be construed as limiting.

EXAMPLE 1

1-[4-Hydroxy-$N^2$-(10,12-dimethyl-1-oxotetradecyl)ornithine]-4-[3-hydroxyhomotyrosine]-5-[3-hydroxyglutamine]echinocandin B hydroxyglutamine)echinocandin B (compound of formula A—2, $X_1$=OH, $X_2$=OH, Z is 9,11-dimethyltridecyl) was dissolved in 5 ml of trifluoroacetic acid and 307 mg (4.89 mmol) of sodium cyanoborohydride was immediately added. The resultant solution was stirred at room temperature for 30 minutes. The mixture was then subjected to reduced pressure to remove the solvents and to recover a white solid residue. The latter was purified by reverse phase HPLC (2.12×25 cm C8 "Zorbax" (Dupont) column) using water/acetonitrile (45/55) at 10 mL/min and lyophilizing the appropriate eluate fractions as determined by NMR to obtain 410 mg (44% yield) of 1-[4-hydroxy-$N^2$-(10,12-dimethyl-1-oxotetradecyl)-ornithine]-4-[3-hydroxyhomotyrosine]-5-[3-hydroxyglutamine]echinocandin B as a white solid having the following spectral properties:

$^1$H—NMR (300 MHz, CD$_3$OD): δ7.02 (d, J=8 Hz, 2H), 3.76 (dd, J=15, 3 Hz, 1H), 2.99 (dd, J=15, 3 Hz, 1H).

Mass spectrum (FAB): 1047 (M+1).

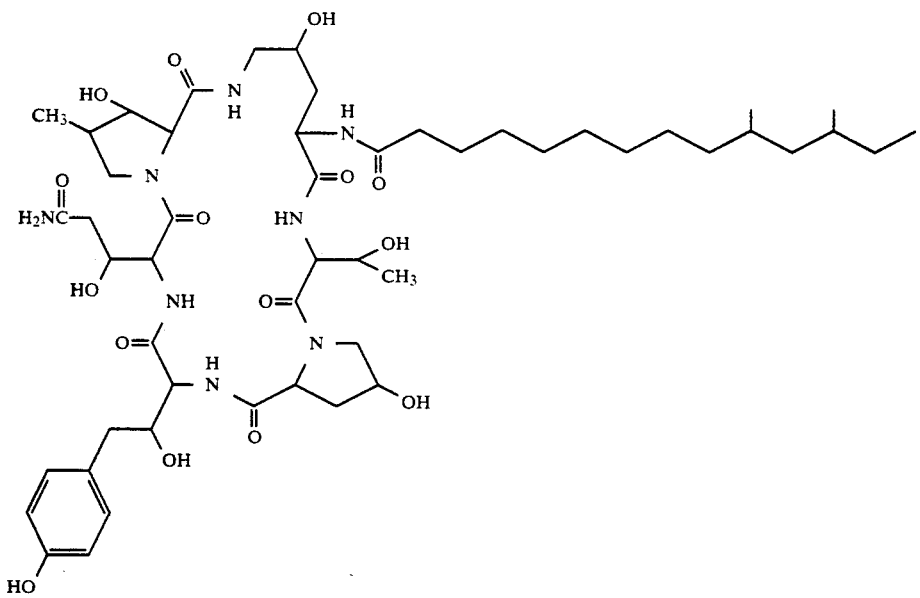

1.02 grams (0.90 mmol) of 1-[4,5-dihydroxy-$N^2$-(10,12-dimethyl-1-oxotetradecyl)ornithine]-5-(3-

EXAMPLE 2

1-[4-Hydroxy-$N^2$-(10,12-dimethyl-1-oxotetradecyl)ornithine]-4-[3-hydroxyhomotyrosine]-5-[3-hydroxyglutamine]-6-[3-hydroxyproline]echinocandin B

EXAMPLE 3

1-[4-Hydroxy-$N^2$-(1-oxooctadecyl)ornithine]-4-[3-hydroxy-homotyrosine]echinocandin B

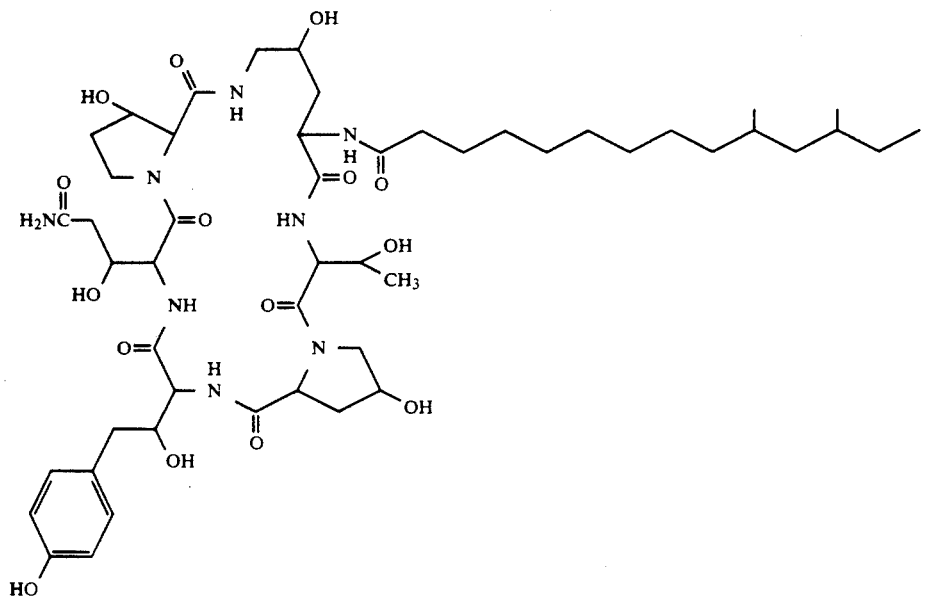

A sample of Compound A—1 (Q=OH, $X_1$=OH, $X_2$=OH, Z=9,11-dimethyltridecyl) of 77% purity (175 mg, 0.16 mmol) was dissolved in 1.0 ml of trifluoroacetic acid. To it was added 75 mg (1.2 mmol) of sodium cyanoborohydride and the solution was stirred at room temperature for 30 minutes. At the end of this period, the volatiles were removed in vacuo to produce a solid. The solid was purified by reverse phase HPLC (C8 "Zorbax") eluting with water/acetonitrile (45/55) at a rate of 10 milliliters per minute to obtain 80 mg (98% pure, 60% yield) of a product having the above formula as a white solid.

$^1$H—NMR (300 MHz, CD$_3$OD): δ7.02 (d, J=8 Hz, 2H), 2.99 (dd, J=15, 3 Hz, 1H).

Mass spectrum (FAB): 1033 (M+1).

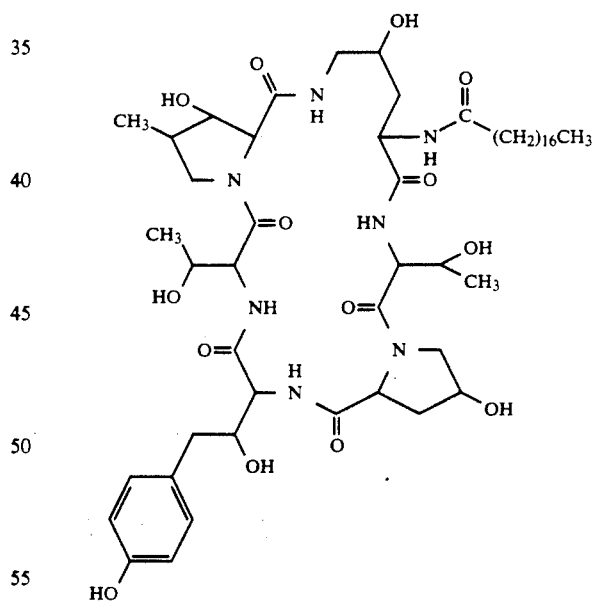

500 mg (0.470 mmol) of tetrahydroechinocandin B (formula A-3, $X_1$=$X_2$=OH, Q=OH, Z=—(CH$_2$)$_{16}$CH$_3$) was suspended in 48 mL of dichloromethane and to it was added 2.3 mL, (30.9 mmol) of trifluoroacetic acid whereupon the reaction mixture became homogeneous. To it was immediately added 333 mg (5.30 mmol) of sodium cyanoborohydride in a single portion whereupon a vigorous evolution of hydrogen gas occurred. After several minutes, the reaction subsided and the mixture was stirred at room temperature for 2 hours. Methanol (15 ml) was added and was followed by removal of the volatiles in vacuo at 30° C. The resultant solid residue was divided into two equal portions and purified separately by reverse phase HPLC (2.12×25 cm C8 "Zorbax") employing $H_2O/CH_3CN$ (30/70) at 10 mL/min and collecting 20 ml fractions. The fractions were lyophilized. The desired 1-[4-hydroxy-$N^2$-(-1-oxooctadecyl)ornithine]-4-[3-hydroxyhomotyrosine]echinocandin B product was obtained in two purities as a fluffy white solid, 200 mg of 98% pure product in a yield of 41% and 170 mg of 95% pure material in a yield of 35%.

$^1$H-NMR (300 MHz, $CD_3OD$): δ7.03 (d, J=9 Hz), 3.70 (dd, J=14, 3.0 Hz), 2.97 (dd, J=14, 3.9 Hz).

Mass Spectrum (FAB, Li+ spike): 1038.

EXAMPLE 4

1-[4-Hydroxy-$N^2$-(1-oxo-octadeca-9,12-dienyl)ornithine]-4-[3-hydroxyhomotyrosine]echinocandin B 40 mg (0.62 mmol) of sodium cyanoborohydride was added to a solution of 100 mg (0.0943 mmol) of echinocandin B (formula A-3, Q=OH, $X_1=X_2=OH$, Z=8,11-heptadecadienyl) in 1.0 mL of trifluoroacetic acid and the mixture was stirred for 45 minutes. At the end of this period, the volatiles were removed in vacuo and the residue was purified by reverse phase HPLC (0.92×25 cm C8 "Zorbax" water/acetonitrile (46/54), 3 mL/min) and the eluates lyophilized to obtain 8 mg (8%) of the desired compound 1-[4-hydroxy-$N^2$-(1-oxooctadeca-9,12-dienyl)ornithine]-4-[3-hydroxyhomotyrosine]echinocandin B as a white solid. $^1$H-NMR (300 MHz, $CD_3OD$): δ7.01 (d, J=8 Hz, 2H), 5.33 (m, 4H), 3.68 (dd, J=14, 3.4 Hz, 1H), 2.96 (dd, J=14, 4.0 Hz, 1H).

Mass Spectrum (FAB): 1028.

EXAMPLE 5

1-[4-Hydroxy-$N^2$-p-(n-octyloxy)benzoylornithine]-4-[3-hydroxyhomotyrosine]echinocandin B

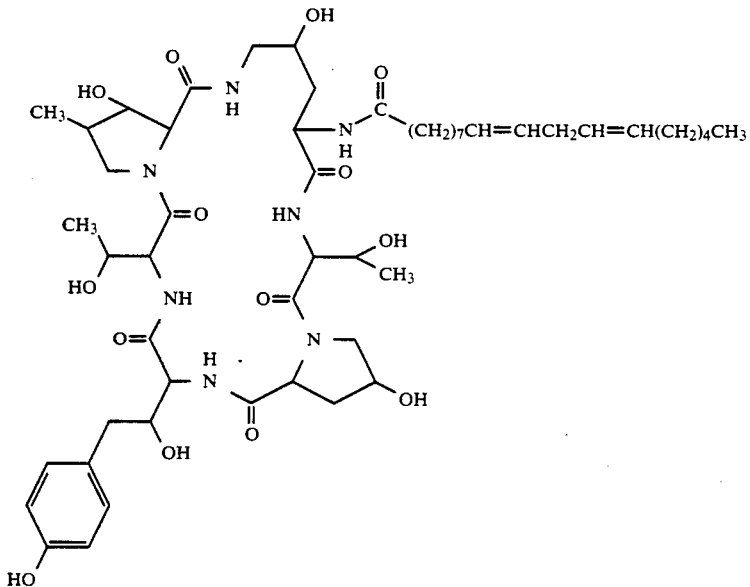

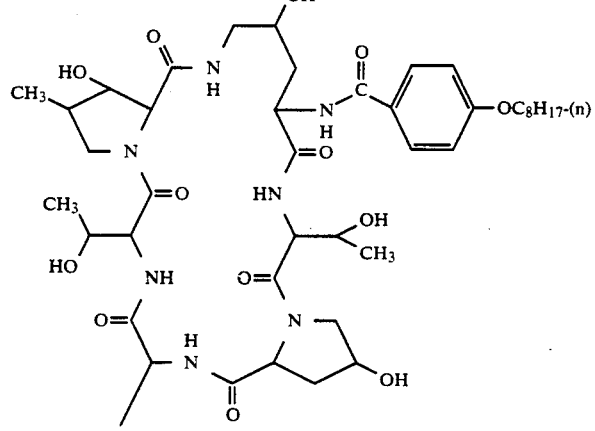

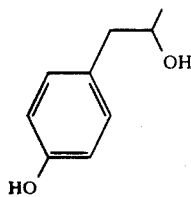

21 milligrams (0.021 mmol) of 1-[4,5-dihydroxy-$N^2$-p-(n-octyloxy)benzoylornithine]echinocandin B ("Cilofungin" (Eli Lilly)) was suspended in 2.0 mL of dichloromethane and to it was added, 0.10 mL (1.3 mmol) of trifluoroacetic acid. To the resulting homogeneous reaction mixture was added in one portion, 14 mg (0.22 mmol) of sodium cyanoborohydride. After stirring at room temperature for 2 hours, a small amount of methanol was added and the volatiles were removed in vacuo. The resultant solid was purified by HPLC (0.92×25 cm C8 "Zorbax") using water/acetonitrile (50/50). Fractions 22–27 which contained the bulk of the product as determined by UV absorption at 268 nm were lyophilized to obtain 10.9 mg (54%) of 1-[4-hydroxy-$N^2$-p-(n-octyloxy)benzoylornithine]-4-[3-hydroxyhomotyrosine]echinocandin B as a fluffy white solid.

$^1$H-NMR (300 MHz, CD$_3$OD): δ7.02 (d, J=9 Hz), 3.72 (dd, J=14, 3.7 Hz), 2.95 (dd, J=14, 4.8 Hz).

Mass Spectrum (FAB): 998 (M+1).

EXAMPLE 6

1-[4-Hydroxy-$N^2$-(1-oxooctadecyl)ornithine]echinocandin B

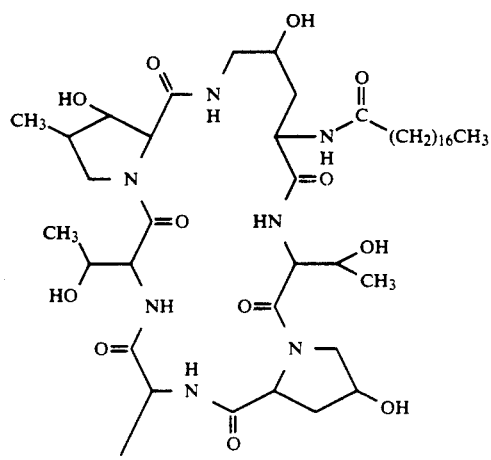

-continued

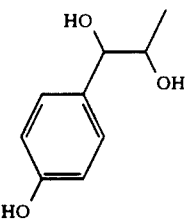

100 mg (0.1 mmol) of tetrahydroechinocandin B was dissolved in 25 mL of glacial acetic acid and to it was added 0.30 mL (4.0 mmol) of trifluoroacetic acid. 60 mg (1.0 mmol) of sodium cyanoborohydride was then added and the mixture stirred at room temperature for 4 hours. Analytical HPLC at this point indicated partial completion of the reaction. The volatiles were removed in vacuo and the residue purified by reverse phase chromatography in a manner similar to that previously described, to obtain 16 mg (16% yield) of the product of the above formula along with some of the bis-reduced product (compound of Example 3).

$^1$H-NMR (300 MHz, CD$_3$OD): δ7.16 (d, J=9 Hz, 2H), 3.67 (dd, J=14, 3 Hz, 1H), 2.97 (dd, J=14, 4 Hz, 1H).

Mass Spectrum (FAB): 1048.

EXAMPLE 7

1-[4-Hydroxy-$N^2$-(10,12-dimethyl-1-oxo-tetradecyl)ornithine]-5-[3-hydroxyglutamine]echinocandin B

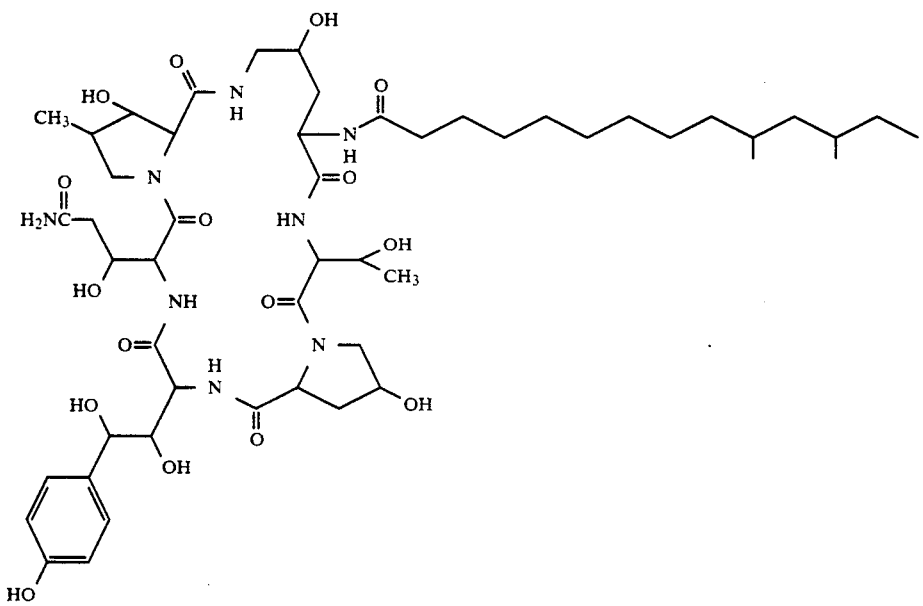

201.6 mg (0.19 mmol) of Compound A-1 (Z=9,11-dimethyltridecyl) was dissolved in 5.0 ml of glacial acetic acid. To the resulting solution was added 2.0 ml (26 mmol) of trifluoroacetic acid followed by 124.6 mg (1.98 mmol) of sodium cyanoborohydride as a solid. After 105 minutes, the mixture was concentrated to obtain a solid. The solid was purified by preparative HPLC ("Zorbax" C8) using water/acetonitrile (45/55) as eluant to obtain several products: two monoreduced products and a bis reduced product.

The monoreduced products were stirred in methanol containing a trace of p-toluenesulfonic acid for several hours. At this time the mixture was concentrated and then purified by preparative HPLC and the eluates then concentrated and lyophilized to obtain the desired monoreduction product, Compound Ib (Z=9,11-dimethyltridecyl).

$^1$H-NMR (300 MHz, CD$_3$OD): δ7.16 (d, J=9 Hz, 1H), 6.77 (d, J=9 Hz, 1H), 3.73 (dd, J=9, 2 Hz, 1H), 2.98 (dd, J=9, 2 Hz, 1H).

Mass Spectrum (FAB): 1063 (M+1).

EXAMPLE 8

In operations carried out in a manner similar to that described in Example 1-5, the compounds in Table I may be prepared.

TABLE I

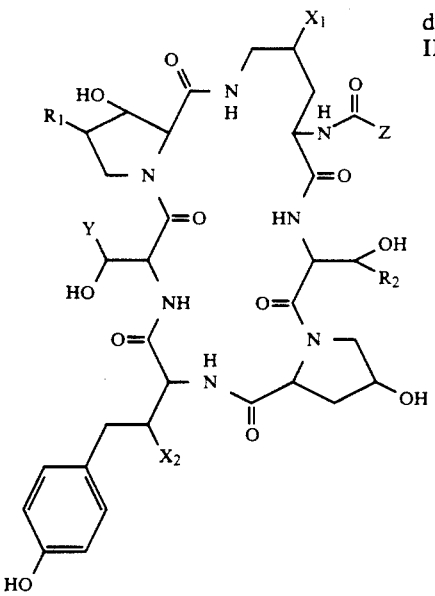

|     | $R_1$ | $R_2$ | $X_1$ | $X_2$ | Y | Z |
|-----|-----|-----|-----|-----|---|---|
| (1) | $CH_3$ | $CH_3$ | OH | OH | $CH_2CONH_2$ | $-C_{13}H_{27}(n)$ |
| (2) | $CH_3$ | $CH_3$ | OH | OH | $CH_2CONH_2$ | $-C_{15}H_{31}(n)$ |
| (3) | $CH_3$ | $CH_3$ | OH | OH | $CH_2CONH_2$ | $-C_{17}H_{35}(n)$ |
| (4) | $CH_3$ | $CH_3$ | OH | OH | $CH_2CONH_2$ | $-C_{19}H_{39}(n)$ |
| (5) | $CH_3$ | $CH_3$ | OH | OH | $CH_2CONH_2$ | $-(CH_2)_7CH=CHCH_2CH=CH(CH_2)_4CH_3$ |
| (6) | $CH_3$ | $CH_3$ | OH | OH | $CH_2CONH_2$ | $-(CH_2)_4CH=CH(CH_2)_{10}CH_3$ |
| (7) | $CH_3$ | $CH_3$ | OH | OH | $CH_2CONH_2$ | $-(CH_2)_{11}CH=CH(CH_2)_7CH_3$ |
| (8) | $CH_3$ | $CH_3$ | OH | OH | $CH_3$ | $-C_6H_4O(CH_2)_7CH_3$-m |
| (9) | $CH_3$ | $CH_3$ | OH | OH | $CH_3$ | $-C_6H_4S(CH_2)_6CH_3$-p |
| (10) | $CH_3$ | $CH_3$ | OH | OH | $CH_3$ | $-C_6H_4S(CH_2)_8CH_3$-p |
| (11) | $CH_3$ | $CH_3$ | OH | OH | $CH_3$ | $-C_6H_4(CH_2)_8CH_3$-p |
| (12) | $CH_3$ | $CH_3$ | OH | OH | $CH_3$ | $-(CH_2)_{12}CH_3$ |
| (13) | $CH_3$ | $CH_3$ | OH | OH | $CH_3$ | $-(CH_2)_7CH=CH(CH_2)_7CH_3$ |

EXAMPLE 9

In operations carried out in a manner similar to that described in Examples 6 and 7, the compounds in Table II may be prepared.

TABLE II

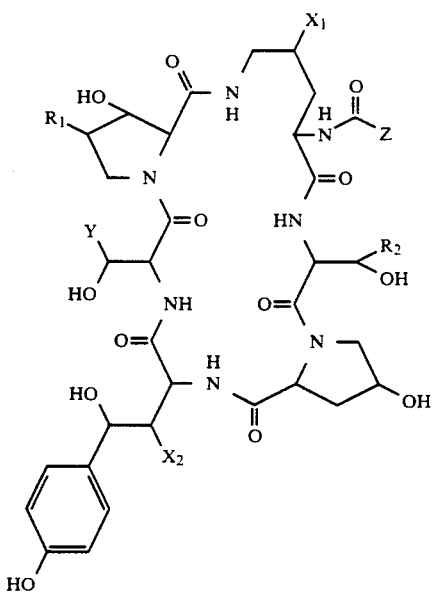

|  | $R_1$ | $R_2$ | $X_1$ | $X_2$ | Y | Z |
|---|---|---|---|---|---|---|
| (1) | $CH_3$ | $CH_3$ | OH | OH | $CH_2CONH_2$ | $-C_{13}H_{27}(n)$ |
| (2) | $CH_3$ | $CH_3$ | OH | OH | $CH_2CONH_2$ | $-C_{15}H_{31}(n)$ |
| (3) | $CH_3$ | $CH_3$ | OH | OH | $CH_2CONH_2$ | $-C_{17}H_{35}(n)$ |
| (4) | $CH_3$ | $CH_3$ | OH | OH | $CH_2CONH_2$ | $-C_{19}H_{39}(n)$ |
| (5) | $CH_3$ | $CH_3$ | OH | OH | $CH_2CONH_2$ | $-(CH_2)_7CH=CHCH_2CH=CH(CH_2)_4CH_3$ |
| (6) | $CH_3$ | $CH_3$ | OH | OH | $CH_2CONH_2$ | $-(CH_2)_4CH=CH(CH_2)_{10}CH_3$ |
| (7) | $CH_3$ | $CH_3$ | OH | OH | $CH_2CONH_2$ | $-(CH_2)_{11}CH=CH(CH_2)_7CH_3$ |
| (8) | $CH_3$ | $CH_3$ | OH | OH | $CH_3$ | $-C_6H_4O(CH_2)_7CH_3$-p |
| (9) | $CH_3$ | $CH_3$ | OH | OH | $CH_3$ | $-C_6H_4S(CH_2)_6CH_3$-p |
| (10) | $CH_3$ | $CH_3$ | OH | OH | $CH_3$ | $-C_6H_4S(CH_2)_8CH_3$-p |
| (11) | $CH_3$ | $CH_3$ | OH | OH | $CH_3$ | $-C_6H_4(CH_2)_8CH_3$-p |
| (12) | $CH_3$ | $CH_3$ | OH | OH | $CH_3$ | $-(CH_2)_{12}CH_3$ |
| (13) | $CH_3$ | $CH_3$ | OH | OH | $CH_3$ | $-(CH_2)_7CH=CH(CH_2)_7CH_3$ |

EXAMPLE 10

1-[4-Hydroxy-$N^2$-p-(n-decanoylamino)benzoylornithine]-4-[3-hydroxyhomotyrosine]echinocandin B

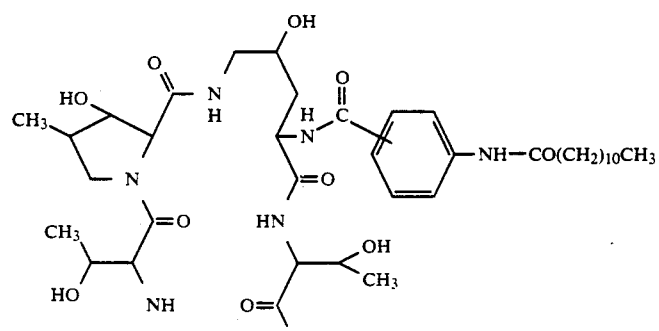

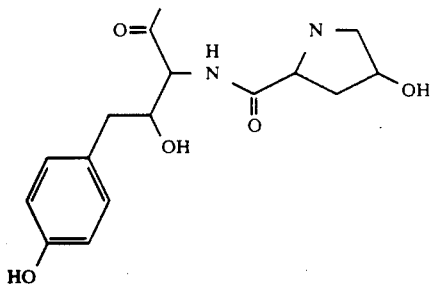

In a manner similar to that described in Example 5, 0.021 millimole of 1-[4,5-dihydroxy-$N^2$-p-(n-decanoylamino)benzoylornithine]echinocandin B is suspended in 2.0 mL of dichloromethane and to it is added, 0.10 mL (1.3 mmol) of trifluoroacetic acid. To the resulting homogeneous reaction mixture is added in one portion, 14 mg (0.22 mmol) of sodium cyanoborohydride. After stirring at room temperature for 2 hours, a small amount of methanol is added and the votaliles removed in vacuo. The residue is purified by HPLC ("Zorbax") using water/acetonitrile (50/50). Fractions which contain the bulk of the product as determined by UV absorption at 268 nm are combined and lyophilized to obtain the desired 1-[4-hydroxy-$N^2$-p-(n-decanoylamino)benzoylornithine]-4-[3-hydroxyhomotyrosine]echinocandin B compound.

Starting Materials

Starting material (A-1) where Z is 9,11-dimethyltridecyl may be obtained by cultivating *Zalerion arboricola* ATCC 20868 or ATCC 20957, in a nutrient medium providing sources of carbon, nitrogen and inorganic salts, preferably in a medium having a polyol, for 7 to 14 days with or without agitation, then recovering the desired metabolite by adding methanol and preferably partitioning into an oxygenated solvent such as ethyl acetate, thereafter removing the solvent and dissolving the residue in a solvent suitable for one or more chromatographic separations and then subjecting the material to such chromatographic separation to separate Compound (A-1) from other metabolites also present. The preparations are more fully described in copending application Ser. No. 374,416, filed Jun. 30, 1989, and copending application Ser. No. 492,025, Ser. No. 492,026, and Ser. No. 492,024, all filed Mar. 12, 1990.

When in Compound (A-1), Z is other than 9,11-dimethyltridecyl, the compound may be prepared first by deacylating Compound (A-1) in which Z is 9,11-dimethyltridecyl by adding a buffered aqueous solution-thereof solubilized with the aid of dimethyl sulfoxide to a resting suspension of washed *Pseudomonas acidovorans* cells in phosphate buffer preferably at pH in the range 6.0 to 7.0, and incubating for 24 hours or longer in the temperature range of 20° to 60° C., and thereafter separating from the fermentation broth by conventional methods such as by centrifuging to separate the cells, charging the supernatant, after first adjusting to pH 7, to a chromatographic column such as "Diaion" SP-207 or HP-20 which has been preequilibrated with methanol/water, followed by washing with methanol/water and eluting with methanol. The eluate containing active material is concentrated and further chromatographed to obtain a deacylated cyclohexapeptide as more fully described and claimed in copending application Ser. No. 492,001, filed Mar. 12, 1990, the teachings of which are incorporated by reference. The deacylated cyclohexapeptide then may be acylated by intimately contacting the cyclohexapeptide with an active ester, ZCOX, where X is an appropriate leaving group such as chloride in a solvent such as dimethylformamide and intimately contacting for 16 to 20 hours at ambient temperature, then recovering the acylated compound by conventional procedures. Compounds in which Z is alkyl, alkenyl, aryl or heteroaryl are described and claimed in copending application Ser. No. 492,012, filed Mar. 12, 1990.

Starting material (A-2) where Z is 9,11-dimethyltridecyl may be obtained by cultivating *Zalerion arboricola* ATCC 20868, in a nutrient medium providing sources of carbon, nitrogen and inorganic salts, preferably in a medium having a polyol for 7 to 14 days with or without agitation, then recovering the desired metabolite by adding methanol and preferably partitioning into an oxygenated solvent such as ethyl acetate, thereafter removing the solvent and dissolving the residue in a solvent suitable for one or more chromatographic separations as described R. E. Schwartz et al., J. antibiotics XLII, No. 2, 163-167 (1989), the structure of which is established by C. F. Wichmann et al., J. Antibiotics XLII, No. 2, 168-173 (1989).

When in Compound (A-2), Z is other than 9,11-dimethyltridecyl, it may be prepared by deacylating the above natural product, (A-2) where Z is 9,11-dimethyltridecyl, with *Pseudomonas acidovorans* in a manner similar to that described for Compound (A-1) and thereafter acylating, also in the manner described for Compound (A-1). When in Compound (A-2), Z is alkyl or alkenyl, the compounds also may be prepared as described in U.S. Pat. No. 4,287,120, Sep. 1, 1981, the teachings of which are incorporated by reference.

Starting material (A-3), when Z is heptadeca-8,11-dienyl, the compound is a natural product first identified by structure by Traber et al., Helv. Chem. Acta 62, 4, 1252-67 (1979) and now known as echinocandin B. The article also describes several other echinocandins and derivatives. Still other derivatives may be obtained by deacylation and acylation as described above for Compounds (A-1) and (A-2). Certain other compounds of the type (A-3) are described in U.S. Pat. No. 4,293,489 which compounds were prepared by acylation of a cyclohexapeptide obtained by enzymatic deacylation of "A-30912 factor A, tetrahydro-A-30912A, or aculeacin A" by an enzyme produced by *Actinoplanes utahensis* as detailed in 4,293,482. The teaching of U.S. Pat. Nos. 4,293,489 and 4,293,482 are incorporated by reference.

Starting compounds A-1, A-2 or A-3 in which Z is alkanoylaminophenyl may be obtained by first deacylating the natural product with *Pseudomonas acidovorans* as described and referenced above and thereafter by acylating with ZCOX as above described. The deacylation also may be carried out with *A. utahensis* that in a manner similar to described by Boeck et al., J. Antibiotics 42, 382(1989) or U.S. Pat. Nos. 4,293,482; 4,293,490; 4,299,762; 4,304,716 and 4,299,763. The ZCOX preferably is a 2,4,5-trichlorophenyl ester of an alkanoylaminobenzoic acid, 3,4,5-trichlorophenol and N,N'-dicyclohexylcarbodiimide in methylene chloride, diethyl ether or tetrahydrofuran and stirring at room temperature, conveniently overnight, thereafter filtering to remove the bulk of the dicyclohexyl urea and concentrating the filtrate and crystallizing from acetonitrile/water. The alkanoylaminobenzoic acid may be synthesized from commercially available or readily preparable from acid chloride and 4-aminobenzoic acid. The synthesis may be carried out by dropwise addition of acid chloride into equimolar amount of the 4-aminobenzoic acid in pyridine and stirring for several hours, thereafter pouring the reaction mixture into water to obtain the alkanoylbenzoic acid as a precipitate. The precipitate is recovered and crystallized in a conventional manner such as from methanol.

Starting materials in which (a) Q is OH, $R_1$ and $R_2$ are $CH_3$, $X_1$ is OH, $X_2$ is H, Y is $-CH_2CONH_2$ and Z is 9,11-dimethyltridecyl and (b) Q is H, $R_1$ and $R_2$ are $CH_3$, $X_1$ and $X_2$ are H, Y is $-CH_2CONH_2$ and Z is 9,11-dimethyltridecyl are natural products which are disclosed and claimed in copending applications Ser. No. 374,418, filed Jun. 30, 1989 now abandoned and Ser. No. 495019 filed Mar. 17, 1990. Derivatives of these compounds in which Z are other groups may be prepared by deacylation of the foregoing natural product and reacylation in the same manner described above as described for Compound (A-1).

Other starting materials which may be employed include (1) sporiofungin A, a natural product in which $R_1$ is $CH_3$, $R_2$ is H, Q is H, Y is $-CH_2CONH_2$ and Z is 9,11-dimethyltridecyl and sporiofungin B in which $R_1$ and $R_2$ and Q are H, Y is $-CH_2CONH_2$ and Z is 9,11-dimethyltridecyl described in the Proceedings of the 13th International Congress of Chemotherapy, Vol 6, 115 (1983); (2) mulundocandin, a natural product in which $R_1$ is H, $R_2$ is $CH_3$, Q is OH, Y is H and Z is 11-methyltridecyl; and (3) semisynthetic derivatives of mulundocandin, and sporiofungin which may be prepared by deacylation of the natural product with *Pseudomonas acidovorans* and thereafter acylating as described above for compound (A-1) or by conventional procedures.

What is claimed is:

1. A method for preparing a compound having the formula

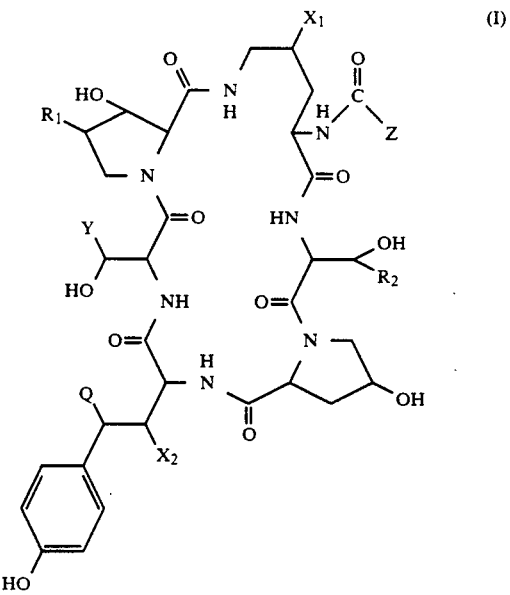

wherein

Q is hydrogen or hydroxyl $R_1$ and $R_2$ are independently hydrogen or methyl $X_1$ and $X_2$ are independently hydrogen or hydroxyl, Y is H—, $CH_3$— or $-CH_2CONH_2$ and Z is (a) a straight or branched chain alkyl from 5 to 23 carbon atoms, (b) a straight or branched chain alkenyl from 5 to 23 carbon atoms, (c) phenyl and substituted phenyl wherein the substituent is $C_1$ to $C_{16}$ alkyl, $C_1$ to $C_{16}$ alkoxy, $C_2$ to $C_{20}$ alkanoylamino, or $C_1$ to $C_{16}$ thioalkoxy; or (d) heteroaryl selected from the group consisting of pyrryl, thiophenyl, furyl, indolyl, benzothiophenyl, benzofuryl, imidazolyl, benzimidazolyl, and pyridinyl, which comprises selectively reducing a compound having the formula

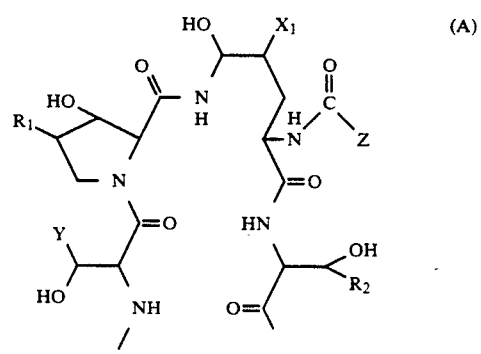

-continued

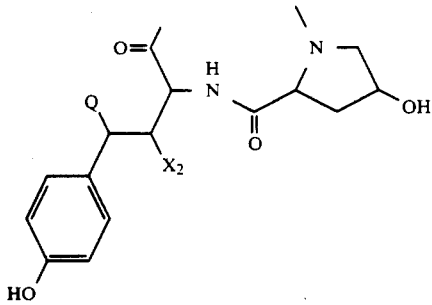

wherein Q, $R_1$, $R_2$, $X_1$, $X_2$, Y and Z are as above defined, in a strong acid medium with about 4 to 10 molar equivalents of sodium cyanoborohydride for time sufficient for reduction of the OH adjacent to $X_1$ to H to take place and when Q is OH, for the reduction of that OH to take place, or in a strong acid medium with about 4 to 10 molar equivalents of sodium cyanoborohydride and glacial acetic acid for time sufficient for the reduction of OH adjacent to $X_1$ to H to take place in the absence of reduction of the OH at Q, and wherein $X_1$ and $X_2$ remain unchanged.

2. A method according to claim 1 in which the strong acid is trifluoroacetic acid or a methylene chloride solution of trichloroacetic acid.

3. A method according to claim 1 wherein a glacial acetic acid or methylene chloride solvent is employed.

4. A method for preparing a compound having the formula

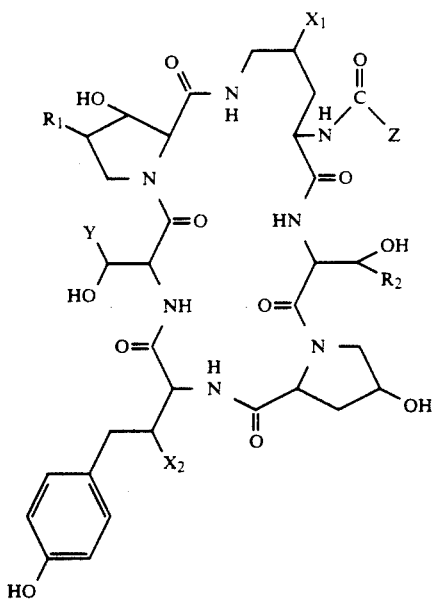

wherein
  $R_1$ and $R_2$ are independently hydrogen or methyl,
  $X_1$ and $X_2$ are independently hydrogen or hydroxyl,
  Y is H—, $CH_3$— or —$CH_2CONH_2$ and
  Z is
    (a) a straight or branched chain alkyl from 5 to 23 carbon atoms,
    (b) a straight or branched chain alkenyl from 5 to 23 carbon atoms,
    (c) phenyl and substituted phenyl wherein the substituent is $C_1$ to $C_{16}$ alkyl, $C_1$ to $C_{16}$ alkoxy, $C_2$ to $C_{20}$ alkanoylamino, or $C_1$ to $C_{16}$ thioalkoxy; or
    (d) heteroaryl selected from the group consisting of pyrryl, thiophenyl, furyl, indolyl, benzothiophenyl, benzofuryl, imidazolyl, benzimidazolyl, and pyridinyl,
which comprises
  (a) intimately mixing a cyclohexapeptide compound having the formula

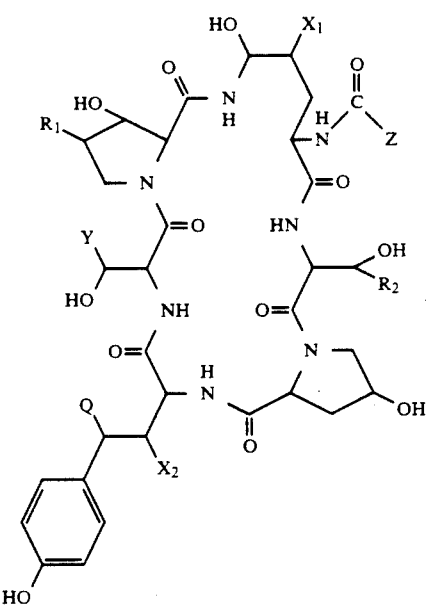

wherein Q is H or OH, and $R_1$, $R_2$, $X_1$, $X_2$, Y and Z are as above defined in a strong acid medium with about 4 to 10 molar equivalents of sodium cyanoborohydride for time sufficient to reduce the OH adjacent to $X_1$ to H, and if Q is OH to reduce that OH to H,
  (b) vaporizing off most of the acid in vacuo,
  (c) subjecting the residue to reverse phase high performance liquid chromatography, and
  (d) lyophilizing the eluate to obtain a solid product; and wherein in the foregoing reactions, $X_1$ and $X_2$ remain unchanged.

5. A method for preparing a compound having the formula

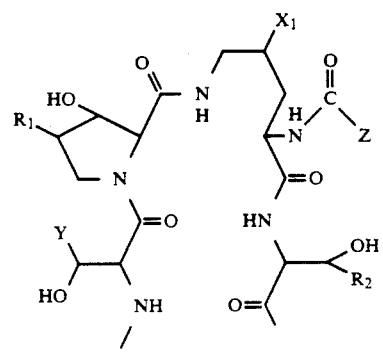

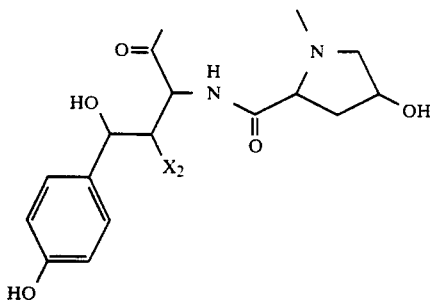

wherein $R_1$ and $R_2$ are independently hydrogen or methyl, $X_1$ and $X_2$ are independently hydrogen or hydroxyl, Y is H—, $CH_3$— or —$CH_2CONH_2$ and Z is (a) a straight or branched chain alkyl from 5 to 23 carbon atoms, (b) a straight or branched chain alkenyl from 5 to 23 carbon atoms, (c) phenyl and substituted phenyl wherein the substituent is $C_1$ to $C_{16}$ alkyl, $C_1$ to $C_{16}$ alkoxy, $C_2$ to $C_{20}$ alkanoylamino, or $C_1$ to $C_{16}$ thioalkoxy; or (d) heteroaryl selected from the group consisting of pyrryl, thiophenyl, furyl, indolyl, benzothiophenyl, benzofuryl, imidazolyl, benzimidazolyl, and pyridinyl, which comprises (a) intimately mixing a cyclohexapeptide compound having the formula

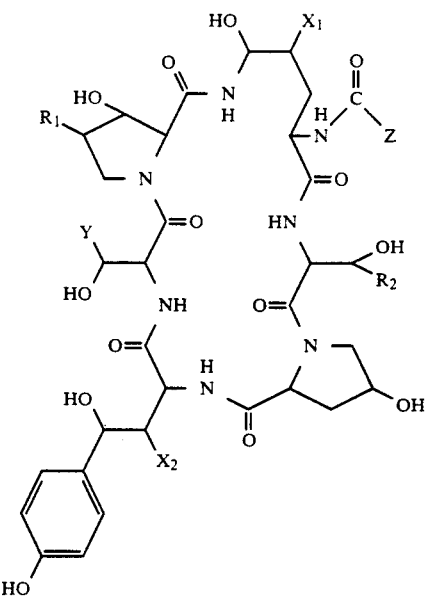

wherein $R_1$, $R_2$, $X_1$, $X_2$, Y and Z are as above-defined in a solvent in a strong acid medium with about 4 to 10 molar equivalents of sodium cyanoborohydride and glacial acetic acid for time sufficient to reduce the OH adjacent to $X_1$ to H, (b) vaporizing off most of the solvent and acid in vacuo, (c) subjecting the residue to reverse phase high performance liquid chromatography, and (d) lyophilizing the eluate to obtain a solid product, wherein in the foregoing reaction $X_1$ and $X_2$ remain unchanged.

* * * * *